United States Patent [19]
Chan et al.

[11] Patent Number: 5,298,029
[45] Date of Patent: Mar. 29, 1994

[54] NITROPHENYLENEDIAMINE DYES HAVING A QUATERNARY CENTER WITH A LONG ALIPHATIC CHAIN

[75] Inventors: Alexander Chan, Mineola, N.Y.; Yuh-Guo Pan, Stanford, Conn.

[73] Assignee: Clairol Incorporated, New York, N.Y.

[21] Appl. No.: 938,783

[22] Filed: Sep. 1, 1992

Related U.S. Application Data

[62] Division of Ser. No. 786,860, Nov. 1, 1991, Pat. No. 5,169,403.

[51] Int. Cl.$^5$ .................. A61K 7/13; C07C 211/46
[52] U.S. Cl. ........................... 8/405; 424/70; 564/305
[58] Field of Search ............. 8/405, 406, 407, 408, 8/410, 414, 416, 423; 424/70; 564/305

[56] References Cited

U.S. PATENT DOCUMENTS 3,893,802  7/1925  Kalopissis et al. .............. 8/416

FOREIGN PATENT DOCUMENTS 1292784  4/1969  Fed. Rep. of Germany .
1127080  9/1968  United Kingdom .

*Primary Examiner*—Paul Lieberman
*Assistant Examiner*—Caroline L. Dusheck
*Attorney, Agent, or Firm*—Morton S. Simon; Doreen F. Shulman

[57] ABSTRACT

Direct dyes having a quaternary center with a long aliphatic chain, compositions containing those dyes, and the process of using them to dye hair are disclosed. These dyes have a higher affinity for hair and are more shampoo stable than conventional direct dyes, and produce pleasing uniform dyeing.

12 Claims, No Drawings

NITROPHENYLENEDIAMINE DYES HAVING A QUATERNARY CENTER WITH A LONG ALIPHATIC CHAIN

This is a continuation, of application Ser. No. 786,860, filed Nov. 1, 1991, now U.S. Pat. No. 5,169,403 entitled DIRECT DYES HAVING A QUATERNARY CENTER WITH A LONG ALIPHATIC CHAIN.

BACKGROUND OF THE INVENTION

This invention relates to direct dyes having a quaternary center with a long aliphatic chain, compositions comprising those dyes, and a process for using those compositions to dye hair.

Direct or semipermanent dyes are very widely used in the field of hair coloring. However, conventional direct dyes have a low affinity for hair and are not very shampoo stable.

Direct dyes having a quaternized amino group are also known. For example, U.S. Pat. No. 3,560,136 (Kalopissis et al.) and U.S. Pat. No. 4,018,556 (Kalopissis et al.) describe compounds of the formula:

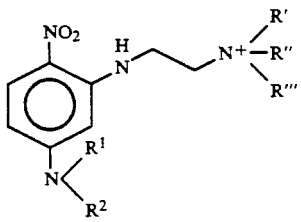

in which R′, R″ and R‴ are $C_{1-4}$ alkyl; and $R^1$ and $R^2$ are each, independently, hydrogen, lower alkyl, $C_{1-6}$ lower hydroxyalkyl, or like substituents.

GB 1,164,824 (Kalopissis et al.) and U.S. Pat. No. 3,978,061 (Kalopissis et al.) describe the above compounds wherein the $NR^1R^2$ group is in the meta-position to the nitro group.

These direct dyes having a quaternary center have a somewhat higher affinity for hair than conventional direct dyes. However, direct dyes having a quaternary center have different affinities for newly grown virgin hair near the root of the hair shaft and for slightly to severely damaged hair along the lower parts of the hair shaft. This hair affinity difference results in aesthetically undesirable uneven dyeing.

Surprisingly, applicants have found that direct dyes having a quaternary center with a long aliphatic chain have a higher affinity for hair and are more shampoo stable than conventional direct dyes, and produce pleasing uniform dyeing that cannot be achieved with direct dyes having just a quaternary center.

SUMMARY OF THE INVENTION

It is an object of this invention to provide a wide color variety of novel direct dye compounds having a quaternary center with a long aliphatic chain, which have a high affinity for hair, are shampoo stable, and produce pleasing uniform dyeing.

It is also an object of this invention to provide novel direct nitroaniline (yellow to orange colors), nitrophenylenediamine (red to violet colors), nitroaminophenol (yellow to red colors), and aminoanthraquinone (violet to blue colors) dye compounds, which have a high affinity for hair, are shampoo stable, and produce uniform dyeing, of the formula (I):

$$Q-NR_6(CH_2)_n-N^+R_1R_2R_3\ X^-$$

or cosmetically acceptable salts thereof, wherein

Q is nitrobenzene, nitroaniline, nitrophenol, or anthraquinone;

n is 2 to 12

$R_1$ is $C_{1-6}$ alkyl, $C_{1-6}$ hydroxyalkyl, or $C_{1-6}$ polyhydroxyalkyl;

$R_2$ is $C_{1-6}$ alkyl, $C_{1-6}$ hydroxyalkyl, or $C_{1-6}$ polyhydroxyalkyl;

$R_3$ is a $C_{8-22}$ aliphatic chain;

$R_6$ is hydrogen, $C_{1-6}$ alkyl, $C_{1-6}$ hydroxyalkyl, or $C_{1-6}$ polyhydroxyalkyl; and $X^-$ is a monovalent or divalent anion.

It is also an object of this invention to provide compositions that comprise direct dye compounds having a quaternary center with a long aliphatic chain and a cosmetically acceptable carrier, which compositions have a high affinity for hair, are shampoo stable, and produce pleasing uniform dyeing.

It is also an object of this invention to provide a process for dyeing hair using compositions comprising novel direct dye compounds having a quaternary center with a long aliphatic chain, which compositions have a high affinity for hair, are shampoo stable, and produce pleasing uniform dyeing.

DETAILED DESCRIPTION OF THE INVENTION

The present invention provides direct nitroaniline (yellow to orange colors), nitrophenylenediamine (red to violet colors), nitroaminophenol (yellow to red colors), and aminoanthraquinone (violet to blue colors) dye compounds of the formula (I):

$$Q-NR_6(CH_2)_n-N^+R_1R_2R_3\ X^-$$

or cosmetically acceptable salts thereof, wherein

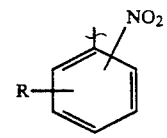 (II)

a nitroaniline of the formula (III):

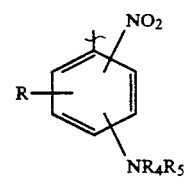 (III)

a nitrophenol of the formula (IV):

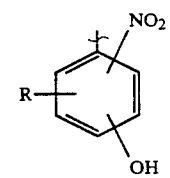 (IV)

or an anthraquinone of the formula (V):

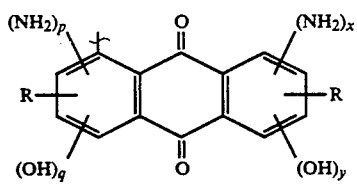

R is hydrogen, $C_{1-6}$ alkyl, $C_{1-6}$ hydroxyalkyl, $C_{1-6}$ polyhydroxyalkyl, halogen, $C_{1-6}$ alkoxy, halogenated $C_{1-3}$ alkyl, polyhalogenated $C_{1-3}$ alkyl, CN, $CONH_2$, $SO_3H$ or COOH;

$R_1$ is $C_{1-6}$ alkyl, $C_{1-6}$ hydroxyalkyl, or $C_{1-6}$ polyhydroxyalkyl;

$R_2$ is $C_{1-6}$ alkyl, $C_{1-6}$ hydroxyalkyl, or $C_{1-6}$ polyhydroxyalkyl;

$R_3$ is a $C_{8-22}$ aliphatic chain;

$R_4$ and $R_5$ are:

independent of each other, hydrogen, $C_{1-6}$ alkyl; $C_{1-6}$ hydroxyalkyl, or $C_{1-6}$ polyhydroxyalkyl, or together with N, a 5 or 6 member heterocyclic ring, $R_6$ is hydrogen, $C_{1-6}$ alkyl, $C_{1-6}$ hydroxyalkyl, or $C_{1-6}$ polyhydroxyalkyl;

n is 2-12; and p, q, x, and y are, independent of each other, 0, 1, or 2.

The preferred nitroaniline dye compounds of this invention are compounds of the formula (IIa):

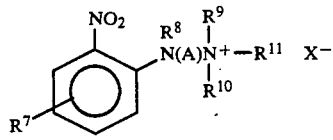

or cosmetically acceptable salts thereof, wherein $R^7$ is hydrogen, $C_{1-6}$ alkyl, $C_{1-6}$ hydroxyalkyl, $C_{1-6}$ polyhydroxyalkyl, halogen, halogenated alkyl, cyano, $CONH_2$, COOH, or $SO_3H$;

$R^8$ is hydrogen, $C_{1-6}$ alkyl, $C_{1-6}$ hydroxyalkyl, or $C_{1-6}$ polyhydroxyalkyl;

A is $C_{2-6}$ alkylene;

$R^9$ is $C_{1-6}$ alkyl, $C_{1-6}$ hydroxyalkyl, or $C_{1-6}$ polyhydroxyalkyl;

$R^{10}$ is $C_{1-6}$ alkyl, $C_{1-6}$ hydroxyalkyl, or $C_{1-6}$ polyhydroxyalkyl;

$R^{11}$ is a $C_{8-22}$ aliphatic chain; and $X^-$ is a monovalent or divalent anion.

The $C_{1-6}$ alkyl or $C_{1-6}$ hydroxyalkyl groups that are represented by $R^9$ or $R^{10}$ include methyl, ethyl, and hydroxyethyl.

The monovalent or divalent anion that is represented by $X^-$ includes halide, hydroxide, and sulfate.

The more preferred nitroaniline dye compounds of this invention are compounds of the formula (IIb):

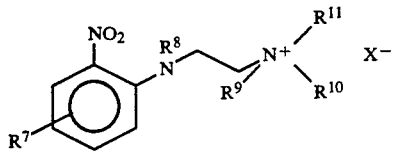

or cosmetically acceptable salts thereof, wherein
$R^7$ is hydrogen or methyl;

$R^8$ is hydrogen or methyl;

$R^9$ is methyl or ethyl;

$R^{10}$ is methyl or ethyl;

$R^{11}$ is $C_{8-22}$ alkyl; and $X^-$ is iodide, bromide, or chloride.

The most preferred nitroaniline dye compounds of this invention are compounds of formula (IIb), wherein $R^7$ is hydrogen, 4-methyl, or 5-methyl;

$R^8$ is hydrogen;

$R^9$ is methyl or ethyl;

$R^{10}$ is methyl or ethyl;

$R^{11}$ is $C_{12-18}$ alkyl; and $X^-$ iodide or bromide.

Nitroaniline dye compounds of this invention include dye compounds of the formulae:

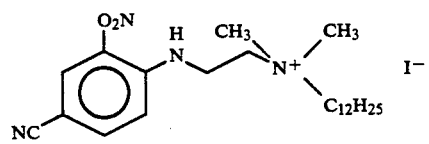

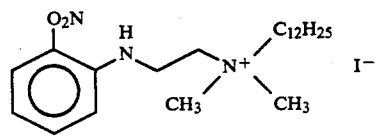

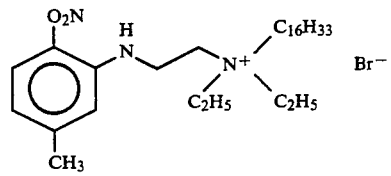

Nitrophenylenediamine dye compounds of this invention include dye compounds of the formulae:

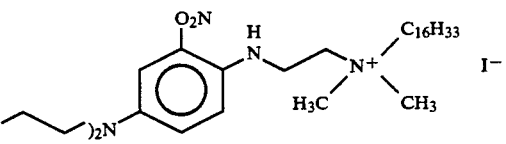

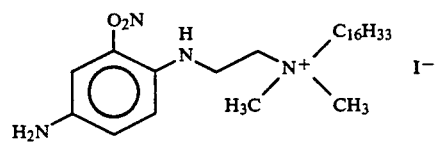

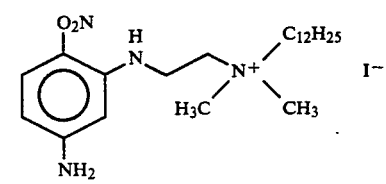

Nitroaminophenol dye compounds of this invention include dye compounds of the formulae:

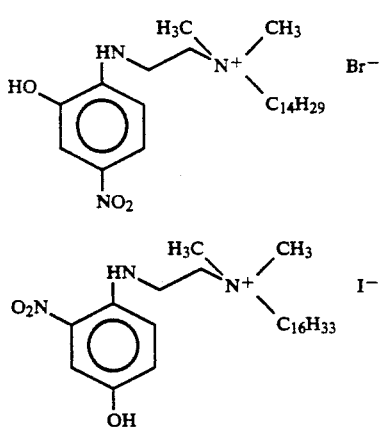

Aminoanthraquinone dye compounds of this invention include dye compounds of the formulae:

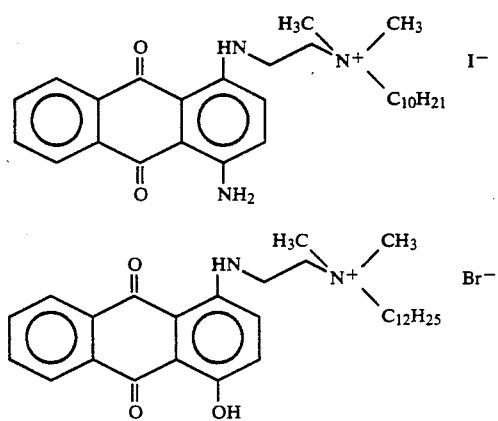

The process for synthesizing the dye compounds of this invention is exemplified by the following procedure: react, in acetonitrile, N,N-dialkylalkylenediamine with a fluoronitrobenzene derivative; pour the reaction mixture into ice water to precipitate the intermediate; isolate the intermediate by filtration; dissolve the isolated intermediate in a solution of acetonitrile containing an equimolar amount of alkyl halide to form a precipitate that is the dye compound of this invention; and isolate the precipitate by filtration. The yield of final precipitate from this reaction is usually greater than 80%. The structure of the isolated precipitate may be determined by nuclear magnetic resonance and mass spectroscopy.

This invention also provides dye compositions that comprise:

(a) a tinctorially effective amount of at least one dye compound of formula (I), or a cosmetically acceptable salt thereof, and (b) a cosmetically acceptable carrier that is compatible with the dye compound of formula (I).

The amount of dye compound required in the compositions of this invention will vary according to factors such as the carrier used, the presence of other hair dyes in the composition, and the desired hair color. Thus, a tinctorially effective amount of dye compound should be used. In general, however, the amount of dye compound required will be about 0.01% to about 10% by weight, but preferably about 0.1% to about 5% by weight, of the composition.

The cosmetically acceptable carriers that may be used in accordance with this invention vary from simple solutions or dispersions with aqueous or alcoholic solvents, to complex mixtures that contain thickening agents. The carriers that may be used in accordance with this invention should be compatible with a dye compound of formula (I). Water will ordinarily be the main component of the carriers that may be used with this invention. The amount of water in the dye compositions of this invention will vary according to the types and quantities of adjuvants or additives in the composition. Thus, the dye composition may contain only about 10% by weight of water, but will usually contain about 70% to about 90% by weight of water.

In addition to a cosmetically acceptable carrier, it may be desirable to include in the hair dye compositions of this invention adjuvants or additives that are commonly found in hair dye compositions and that are compatible with a dye compound of formula (I), in amounts effective to provide their intended function. Such adjuvants or additives include solvents, surface active agents, thickening agents, alkalizing agents, chelating agents, and perfumes.

The solvents that may be used include organic solvents or solvent systems that solubilize the dyes, adjuvants, or additives in the dye compositions of this invention. A number of organic solvents are known in the art that are useful for such purposes. These organic solvents include alcohols, particularly alkyl alcohols of 1-6 carbons, especially ethanol and propanol; and glycols of up to about 10 carbons, especially diethyleneglycol, monobutyl ether, carbitols, and benzyl alcohol. When present, the solvents will constitute from about 1% to about 60% by weight, but preferably from about 10% to about 30% by weight, of the total dye composition.

The surface active agents that may be used in the compositions of this invention are typically water soluble, less preferably water dispersible, and include anionic, nonionic, or cationic surface active agents. Such water soluble surface active agents include: higher alkyl benzene sulfonates; alkyl naphthalene sulfonates; sulfonated esters of alcohols and poly acids; taurates; fatty alcohol sulfates; sulfates of branched chain or secondary alcohols; and alkyl dimethylbenzyl ammonium chlorides.

Specific surface active agents that may be used in the compositions of this invention include: cocobetaine; polyquaternium 6; dodecyltrimethylammonium chloride; stearylkonium chloride; lauryl sulfate; polyoxyethylene lauryl ester; myristyl sulfate; glyceryl monostearate; sodium salt of palmitic acid; methyl taurine; cetyl pyridinium chloride; lauryl sulfonate; myristyl sulfonate; lauric diethanolamide; polyoxyethylene stearate; stearyl dimethyl benzyl ammonium chloride; dodecyl benzene sodium sulfonate; nonyl naphthalene sodium sulfonate; dioctylsodium sulfosuccinate; and sodium dodecyl sulfate. The quantity of water soluble surface active agent used can be up to about 15% by weight of the dye composition, but is preferably from about 0.10% to 10% by weight of the dye composition.

The thickening agents that may be used in the compositions of this invention include: polyvinylpyrrolidone, sodium alginate, gum arabic, cellulose derivatives such as methylcellulose or the sodium salt of carboxymethylcellulose, acrylic polymers such as polyacrylic acid sodium salt, and inorganic thickeners such as bentonite. The amount of thickening agent that can be used is about 20% by weight, but preferably about 0.1% to 5% by weight, of the dye composition.

The dye compositions of this invention may also contain other dye compounds. Such other compounds include conventional oxidation dyes, such as p-phenylenediamine, α-naphthol, p-aminophenol, m-aminophenol, resorcinol, m-phenylenediamine, and their derivatives, in the presence of a conventional oxidizer, such as hydrogen peroxide. Such other compounds also include conventional direct dyes, including o- and p-nitroanilines, nitro-p-phenylenediamines, aminoanthraquinones, aminoazobenzenes, and their derivatives. Such other compounds further include the direct dye compounds having a quaternary center with a long aliphatic chain of this invention.

The dye compositions of this invention may be prepared by methods known in the art. For example, the dye can be dissolved or dispersed in water; the dye can be solubilized with water miscible organic solvents; and the dye composition ingredients may be dispersed by heating.

The present invention also provides a process for dyeing hair that comprises applying to the hair a dye composition that comprises:

(a) a tinctorially effective amount of at least one dye compound of formula (I), or a cosmetically acceptable salt thereof, and (b) a cosmetically acceptable carrier that is compatible with the dye compound of formula (I).

The dye compositions may be applied to hair by conventional techniques known in the art. For example, they can be poured over the hair or applied with an applicator. The amount of time for which the dye composition must be in contact with the hair is not critical. It may vary from about 5 minutes to about 2 hours, but is usually from about 10 minutes to about 1 hour. Hair may be dyed at temperatures between about 15° C. and about 40° C., but is preferably dyed at ambient room temperatures of about 20° C. to about 35° C.

The following examples are illustrative of the present invention and shall not be construed as limiting the scope of this invention in any manner.

EXAMPLE 1

A tress of blended gray hair was treated for 30 minutes with a composition containing 0.2 g nitroaniline dye compound 1a of formula (I): dimethylhexadecyl-2-(2-nitroanilino)ethylammonium iodide; 65 g 95% ethyl alcohol; water qs 100 g of composition; and ammonium hydroxide qs pH 7. The tress was then shampooed, rinsed with water, and dried. The resulting tress had a bright yellow color.

EXAMPLE 2

A tress of Piedmont hair was treated for 30 minutes with a composition containing 0.2 g nitroaniline dye compound 2a of formula (I): diethyl-2-(2-nitroanilino)ethyl tetradecylammonium iodide; 65 g 95% ethyl alcohol; water qs 100 g of composition; and ethanolamine qs pH 10. The tress was then shampooed, rinsed with water, and dried. The resulting tress had a bright yellow color.

EXAMPLE 3

A tress of Piedmont hair was treated for 30 minutes with a composition containing 0.2 g nitroaniline dye compound 3a of formula (I): dimethylhexadecyl-2-(5-methyl-2-nitroanilino)ethylammonium bromide: 65 g 95% ethyl alcohol; water qs 100 g of composition; and ethanolamine qs pH 10. The tress was then shampooed, rinsed with water, and dried. The resulting tress had a bright yellow color.

EXAMPLE 4

A tress of Piedmont hair was treated for 30 minutes with a composition containing 2% by weight of a nitroaniline dye compound of formula (I): dimethyloctadecyl-2-(4-cyano-2-nitroanilino)ethylammonium iodide; water qs 100 g of composition; and ammonium hydroxide qs pH 9.5. The tress was then shampooed, rinsed with water, and dried. The resulting tress had a bright yellow color.

EXAMPLE 5

A tress of Piedmont hair was treated for 30 minutes with a composition containing 1 g nitroaniline dye compound 1a of formula (I); 13.60 g diethylene glycol monoethyl ether; 2.50 g cocamide; 2.50 g PEG-8 tallow amine; 4.33 g octoxynol-1; 6 g nonoxynol-4; 9.33 g nonoxynol-9; 38.50 g 95% ethyl alcohol; and water qs 100 g of composition [pH 9]. The tress was then shampooed, rinsed with water, and dried. The resulting tress had a bright yellow color.

EXAMPLE 6

A tress of blended gray hair was treated for 30 minutes with the following composition. 0.10% dye compound 3a of formula (I), 0.11% p-phenylenediamine (an oxidation dye intermediate), and 0.14% α-naphthol (an oxidation dye coupler) were dissolved in a 3:2 alcohol/water mixture. Two parts of this solution were mixed with one part of 30 volume hydrogen peroxide and the pH of the final solution was adjusted to 9.9 with $NH_4OH$ solution. The tress was them shampooed, rinsed with water, and dried. The resulting tress had an ash brown color.

EXAMPLE 7

A tress of blended gray hair was treated for 30 minutes with a composition containing 1.5% by weight of a nitrophenylenediamine dye compound of formula (III): dimethyloctadecyl-2-[4-bis(hydroxyethyl)amino-2-nitroanilino] ethylammonium iodide; 57% by weight ethyl alcohol; water qs 100 g of composition; and ammonium hydroxide qs pH 9.0. The tress was then shampooed, rinsed with water, and dried. The resulting tress had a red violet color.

EXAMPLE 8

Tresses of Piedmont hair were treated for 30 minutes with compositions comprising a direct quaternized dye with a long aliphatic chain, of formula (I) (compound 1a); a direct quaternized dye (compound 1b): trimethyl-2-(2-nitroanilino)ethylammonium iodide; and a direct dye (compound 1c): N-(2-hydroxyethyl)-2-nitroaniline. All of the tresses were dyed yellow. The hair affinity and shampoo stability of these dye compounds were determined by shaking the dyed tresses in shampoo solution for 135 minutes and, using the Hunter L,a,b Color Scale, measuring the change in hair color due to dye removal, over time. In the Hunter L,a,b Color Scale system, "L" is a measure of lightness and varies from 100 for perfect white to zero for perfect black. "a" is a measure of redness when the value of "a" is positive and a measure of greeness when negative. "b" is a measure of yellowness when the value of "b" is positive and a measure of blueness when negative. The data from this experiment is recorded in Table I.

Since yellow dyes were used in this Example, the change in the value of "b" (Δb) (the measure of yellow color) between the dyed and shampooed tresses is significant. Δb for compound 1a was 2.3, Δb for compound 1b was 10.5, and Δb for compound 1c was 4.8. This demonstrates that the yellow color was removed most rapidly from the tresses dyed with compounds 1b and 1c.

Furthermore, the differences between the L,a,b values of the shampooed tresses dyed with compounds 1b or 1c, and the L,a,b value of the undyed tress, are less than the difference between the L,a,b value of the shampooed tress dyed with compounded 1a, and the L, a, b value of the undyed tress. Thus, it can be seen that the composition comprising dye compound 1a of formula (I) had the highest affinity for hair and was the most shampoo stable.

TABLE I

CHANGES IN COLOR
(HUNTER L,a,b COLOR SCALE VALUES)

| Dye Compound | Treatment Stage | L | a | b |
|---|---|---|---|---|
| 1a | Dyed | 55.0 | −4.0 | 28.7 |
| | Shampooed | 54.8 | −4.8 | 26.4 |
| 1b | Dyed | 50.2 | −2.6 | 28.5 |
| | Shampooed | 52.8 | −2.6 | 18.0 |
| 1c | Dyed | 53.2 | −1.2 | 21.1 |
| | Shampooed | 54.5 | −1.5 | 16.3 |
| none | Undyed | 58.9 | 0.5 | 18.0 |

EXAMPLE 9

Tresses of Piedmont hair were treated for 30 minutes with compositions comprising a direct quaternized dye with a long aliphatic chain, of formula (I) (compound 2a); a direct quaternized dye (compound 2b): diethylmethyl-2(2-(2-nitroanilino)ethylammonium iodide: and a direct dye (compound 2c): 1-[2-(N,N-diethylamino)ethyl]amino-2-nitrobenzene. All of the tresses were dyed yellow. The hair affinity and shampoo stability of these dye compounds were determined by measuring the color, using the Hunter L,a,b Color Scale, of each dyed tress, shaking each dyed tress in shampoo solution for 1 hour, and measuring the color of each shampooed tress. "L", "a" and "b" are the same measures previously described. The data for the changes in ΔL, Δa, and Δb of the dyed and shampooed tresses are recorded in Table II.

Since yellow dyes were used in this Example, the change in the value of "Δb" (the measure of yellow color) between the dyed and shampooed tresses is significant. The change in Δb for compound 2a was 1.6, the change in Δb for compound 2b was 9.4, and the change in Δb for compound 2c was 5.9. This demonstrates that the yellow color was removed most rapidly from the tresses dyed with compounds 2b and 2c. Thus, it can be seen that the composition comprising dye compound 2a of formula (I) had the highest affinity for hair and was the most shampoo stable.

TABLE II

CHANGES IN COLOR
(HUNTER L,a,b COLOR SCALE VALUES)

| Dye Compound | Treatment Stage | ΔL | Δa | Δb |
|---|---|---|---|---|
| 2a | Dyed | 6.1 | −2.8 | 13.1 |
| | Shampooed | 7.1 | −3.6 | 11.5 |
| 2b | Dyed | 4.1 | −3.7 | 12.9 |
| | Shampooed | 5.4 | −2.1 | 3.5 |
| 2c | Dyed | 2.1 | −1.9 | 6.2 |
| | Shampooed | 2.2 | −0.2 | 0.3 |

EXAMPLE 10

Tresses of Piedmont hair were treated for 30 minutes with compositions comprising a direct quaternized dye with a long aliphatic chain, of formula (I) (compound 3a); direct quaternized dye (compound 3b): trimethyl-2-(5-methyl-2-nitroanilino)ethylammonium iodide; and direct dye (compound 3c): 1-[2-(N,N-dimethylamino)ethyl]amino-5-methyl-2-nitrobenzene. Each compound had been dissolved in a solution of 1.85 parts ethanol to 1 part water and each composition was adjusted to pH 9. All of the tresses were dyed yellow. The hair affinity and shampoo stability of these dye compounds were determined by measuring the color, using the Hunter L,a,b Color Scale, of each dyed tress, rinsing and shampooing each dyed tress, and measuring the color of each shampooed tress. "L", "a" and "b" are the same measures previously described. The data for the changes in ΔL, Δa and Δb of the dyed and shampooed tresses are recorded in Table III.

Since yellow dyes were used in this Example, the change in the value of "Δb" (the measure of yellow color) between the dyed and shampooed tresses is significant. The change in Δb for compound 3a was 2.4, the change in Δb for compound 3b was 9.1, and the change in Δb for compound 3c was 3.3. This demonstrates that the yellow color was removed most rapidly from the tresses dyed with compounds 3b and 3c. Thus, it can be seen that the composition comprising dye compound 3a of formula (I) had the highest affinity for hair and was the most shampoo stable.

TABLE II

CHANGES IN COLOR
(HUNTER L,a,b COLOR SCALE VALUES)

| Dye Compound | Treatment Stage | ΔL | Δa | Δb |
|---|---|---|---|---|
| 3a | Dyed | −4.6 | −4.7 | 11.9 |
| | Shampooed | −6.8 | −2.9 | 9.5 |
| 3b | Dyed | −2.8 | −2.6 | 13.6 |
| | Shampooed | −2.1 | −2.0 | 4.5 |
| 3c | Dyed | −0.8 | −0.9 | 4.4 |
| | Shampooed | −1.5 | 0.0 | 1.1 |

We claim:

1. A dye composition comprising:
   (a) a tinctorially effective amount of at least one nitrophenylenediamine dye compound of the formula (I):

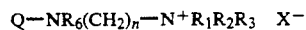

$$Q-NR_6(CH_2)_n-N^+R_1R_2R_3 \quad X^-$$

or cosmetically acceptable salts thereof, wherein Q is a nitroaniline of the formula (III):

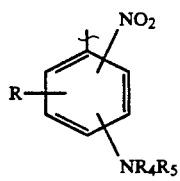

n is 2 or 12;

R is hydrogen, $C_{1-6}$ alkyl, $C_{1-6}$ hydroxyalkyl, $C_{1-6}$ polyhydroxyalkyl, halogen, $C_{1-6}$ alkoxy, halogenated $C_{1-3}$ alkyl, polyhalogenated $C_{1-3}$ alkyl, CN, $CONH_2$, $SO_3H$ or COOH;

$R_1$ is $C_{1-6}$ alkyl, $C_{1-6}$ hydroxyalkyl, or $C_{1-6}$ polyhydroxyalkyl;

$R_2$ is $C_{1-6}$ alkyl, $C_{1-6}$ hydroxyalkyl, or $C_{1-6}$ polyhydroxyalkyl;

$R_3$ is a $C_{8-22}$ aliphatic chain;

$R_4$ and $R_5$ are:

independent of each other, hydrogen, $C_{1-6}$ alkyl; $C_{1-6}$ hydroxyalkyl, or $C_{1-6}$ polyhydroxyalkyl, or together with N, a 5 or 6 member heterocyclic ring, $R_6$ is hydrogen, $C_{1-6}$ alkyl, $C_{1-6}$ hydroxyalkyl, or $C_{1-6}$ polyhydroxyalkyl; and $X^-$ is a monovalent or divalent anion;

(b) a cosmetically acceptable carrier that is compatible with the dye compound of formula (I); and (c) at least one adjuvant or additive selected from the group consisting essentially of surface active agents, alkalizing agents, chelating agents and perfumes.

2. The dye composition of claim 1 wherein the amount of dye compound is about 0.01% to about 10% by weight of the composition.

3. The dye composition of claim 1 further comprising one or more of the following: solvents, surface active agents, thickening agents, alkalizing agents, chelating agents, and perfumes; that are compatible with the dye compound of formula (I).

4. The dye composition of claim 1 further comprising one or more other dye compounds.

5. A process for dyeing hair that comprises applying to the hair a dye composition that comprises:

(a) a tinctorially effective amount of at least one nitrophenylenediamine dye compound of the formula (I):

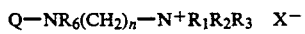

or cosmetically acceptable salts thereof, wherein

Q is a nitroaniline of the formula (III):

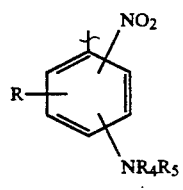

n is 2 or 12;

R is hydrogen, $C_{1-6}$ alkyl, $C_{1-6}$ hydroxyalkyl, $C_{1-6}$ polyhydroxyalkyl, halogen, $C_{1-6}$ alkoxy, halogenated $C_{1-3}$ alkyl, polyhalogenated $C_{1-3}$ alkyl, CN, $CONH_2$, $SO_3H$ or COOH;

$R_1$ is $C_{1-6}$ alkyl, $C_{1-6}$ hydroxyalkyl, or $C_{1-6}$ polyhydroxyalkyl;

$R_2$ is $C_{1-6}$ alkyl, $C_{1-6}$ hydroxyalkyl, or $C_{1-6}$ polyhydroxyalkyl;

$R_3$ is a $C_{8-22}$ aliphatic chain;

$R_4$ and $R_5$ are:

independent of each other, hydrogen, $C_{1-6}$ alkyl; $C_{1-6}$ hydroxyalkyl, or $C_{1-6}$ polyhydroxyalkyl, or together with N, a 5 or 6 member heterocyclic ring, $R_6$ is hydrogen, $C_{1-6}$ alkyl, $C_{1-6}$ hydroxyalkyl, or $C_{1-6}$ polyhydroxyalkyl; and $X^-$ is a monovalent or divalent anion;

(b) a cosmetically acceptable carrier that is compatible with the dye compound of formula (I); and (c) at least one adjuvant or additive selected from the group consisting essentially of surface active agents, alkalizing agents, chelating agents and perfumes.

6. The process of claim 5 wherein the amount of dye compound is about 0.01% to about 10% by weight of the composition.

7. The process of claim 5 wherein the dye composition further comprises one or more of the following: solvents, surface active agents, thickening agents, alkalizing agents, chelating agents, and perfumes; that are compatible with the dye compound of formula (I).

8. The process of claim 5 wherein the dye composition further comprises one or more other dye compounds.

9. The dye composition of claim 1 wherein $R_3$ is a $C_{12-22}$ aliphatic chain.

10. The dye composition of claim 1 wherein $R_3$ is a $C_{12-16}$ aliphatic chain.

11. The process of claim 5 wherein $R_3$ is a $C_{12-22}$ aliphatic chain.

12. The process of claim 5 wherein $R_3$ is a $C_{12-16}$ aliphatic chain.

* * * * *